(12) United States Patent
Sinderby et al.

(10) Patent No.: US 9,968,750 B2
(45) Date of Patent: May 15, 2018

(54) METHOD AND SYSTEM FOR PATIENT-SYNCHRONIZED VENTILATORY ASSIST WITH ENDOTRACHEAL THROUGH-FLOW

(75) Inventors: Christer Sinderby, Toronto (CA); Jennifer Beck, Toronto (CA)

(73) Assignee: ST. MICHAEL'S HOSPITAL, Toronto, Ontario (CA)

( * ) Notice: Subject to any disclaimer, the term of this patent is extended or adjusted under 35 U.S.C. 154(b) by 816 days.

(21) Appl. No.: 13/806,816

(22) PCT Filed: Jun. 29, 2011

(86) PCT No.: PCT/CA2011/000765
§ 371 (c)(1),
(2), (4) Date: Jun. 5, 2013

(87) PCT Pub. No.: WO2012/000096
PCT Pub. Date: Jan. 5, 2012

(65) Prior Publication Data
US 2014/0305434 A1 Oct. 16, 2014

Related U.S. Application Data

(60) Provisional application No. 61/359,951, filed on Jun. 30, 2010.

(51) Int. Cl.
*A61M 16/00* (2006.01)
*A61M 16/04* (2006.01)
(Continued)

(52) U.S. Cl.
CPC ....... *A61M 16/0003* (2014.02); *A61B 5/0488* (2013.01); *A61B 5/087* (2013.01);
(Continued)

(58) Field of Classification Search
CPC ............ A61M 16/042; A61M 16/0463; A61M 16/0475; A61M 16/0477; A61M 16/0484;
(Continued)

(56) References Cited

U.S. PATENT DOCUMENTS

| 4,245,633 | A | * | 1/1981 | Erceg | ................. | A61M 16/104 |
| | | | | | | 128/205.17 |
| 5,161,525 | A | * | 11/1992 | Kimm | ................. | A61M 16/00 |
| | | | | | | 128/204.21 |

(Continued)

FOREIGN PATENT DOCUMENTS

| CA | 2 575 939 | 6/2000 |
| CN | 1 44 0 302 | 9/2003 |

(Continued)

*Primary Examiner* — (Jackie) Tan-Uyen T Ho
*Assistant Examiner* — Joseph D Boecker
(74) *Attorney, Agent, or Firm* — Fay Kaplun & Marcin, LLP

(57) ABSTRACT

A ventilatory assist system and method are disclosed. The system comprises a tube for connection to a patient's airway, inspiratory and expiratory tube lumens connected to the tube, an inspiratory air source connected to the inspiration tube lumen, and a controller of air pressure in the expiratory tube lumen. The pressure controller is responsive to a physiological breathing signal representative of patient's inspiratory effort to allow air flow through the expiratory tube lumen during a patient's expiration phase, partially restricting the air flow through the expiratory tube lumen to a so minimum air flow during a patient's inspiration phase. During both respiratory phases, a unidirectional air flow is produced through the inspiratory and expiratory tube lumens to prevent air expired by the patient from being breathed again. The physiological breathing signal allows synchronization of the ventilatory assist with breathing efforts of the patient.

22 Claims, 6 Drawing Sheets

(51) Int. Cl.
  *A61M 16/10* (2006.01)
  *A61M 16/12* (2006.01)
  *A61M 16/16* (2006.01)
  *A61M 16/20* (2006.01)
  *A61B 5/0488* (2006.01)
  *A61B 5/087* (2006.01)
  *A61B 5/00* (2006.01)

(52) U.S. Cl.
  CPC .......... *A61B 5/4836* (2013.01); *A61M 16/00* (2013.01); *A61M 16/0012* (2014.02); *A61M 16/0051* (2013.01); *A61M 16/0069* (2014.02); *A61M 16/04* (2013.01); *A61M 16/042* (2014.02); *A61M 16/0486* (2014.02); *A61M 16/1005* (2014.02); *A61M 16/12* (2013.01); *A61M 16/125* (2014.02); *A61M 16/161* (2014.02); *A61M 16/202* (2014.02); *A61M 16/205* (2014.02); *A61M 16/024* (2017.08); *A61M 16/16* (2013.01); *A61M 2016/0018* (2013.01); *A61M 2016/0021* (2013.01); *A61M 2016/0027* (2013.01); *A61M 2016/0033* (2013.01); *A61M 2202/0208* (2013.01); *A61M 2210/1014* (2013.01); *A61M 2230/08* (2013.01); *A61M 2230/60* (2013.01)

(58) Field of Classification Search
  CPC .......... A61M 16/0486; A61M 16/0069; A61M 16/009; A61M 16/00; A61M 16/0003; A61M 16/0012; A61M 16/0051; A61M 16/0066; A61M 16/021; A61M 16/022; A61M 16/04; A61M 16/0402; A61M 16/1005; A61M 16/12; A61M 16/125; A61M 16/202; A61M 16/205; A61M 2016/0015; A61M 2016/0018; A61M 2016/0027; A61M 2016/0033; A61B 5/087
  USPC .......................... 128/203.14, 204.18, 204.23
  See application file for complete search history.

(56) References Cited

U.S. PATENT DOCUMENTS

| | | | |
|---|---|---|---|
| 5,291,882 A | | 3/1994 | Makhoul et al. |
| 5,429,123 A | | 7/1995 | Shaffer et al. |
| 5,540,220 A | | 7/1996 | Gropper et al. |
| 5,671,752 A | | 9/1997 | Sinderby et al. |
| 5,797,393 A | * | 8/1998 | Kohl .............. A61M 16/00 128/204.18 |
| 5,820,560 A | | 10/1998 | Sinderby et al. |
| 5,823,184 A | * | 10/1998 | Gross ................ 128/204.18 |
| 5,823,186 A | * | 10/1998 | Rossen et al. ........ 128/204.21 |
| 5,954,051 A | * | 9/1999 | Heinonen .......... A61M 16/00 128/204.21 |
| 6,588,423 B1 | | 7/2003 | Sinderby |
| 6,622,726 B1 | * | 9/2003 | Du .................... A61M 16/00 128/204.21 |
| 6,901,286 B1 | | 5/2005 | Sinderby et al. |
| 7,481,222 B2 | * | 1/2009 | Reissmann ............ 128/207.14 |
| 2002/0020410 A1 | * | 2/2002 | Rydin ............ A61M 16/0051 128/200.24 |
| 2002/0053345 A1 | * | 5/2002 | Jafari ................ A61M 16/00 128/204.23 |
| 2002/0129815 A1 | * | 9/2002 | McPhee ............... 128/200.24 |
| 2003/0075176 A1 | * | 4/2003 | Fukunaga et al. ...... 128/203.12 |
| 2004/0069304 A1 | * | 4/2004 | Jam ..................... 128/204.18 |
| 2004/0221854 A1 | | 11/2004 | Hete et al. |
| 2004/0226559 A1 | * | 11/2004 | Daugherty ............. 128/203.12 |
| 2005/0150505 A1 | * | 7/2005 | Burrow et al. ............ 128/911 |
| 2006/0249153 A1 | * | 11/2006 | DeVries ............ A61M 16/0057 128/204.18 |
| 2007/0062531 A1 | * | 3/2007 | Fisher .................. A61B 5/083 128/204.23 |
| 2007/0062534 A1 | * | 3/2007 | Fisher .................. A61B 5/029 128/205.14 |
| 2007/0144516 A1 | * | 6/2007 | Doyle ............. A61M 16/0883 128/204.18 |
| 2007/0295402 A1 | * | 12/2007 | Awtar et al. .......... 137/119.01 |
| 2008/0060646 A1 | * | 3/2008 | Isaza ............... A61M 16/0468 128/204.21 |
| 2008/0121231 A1 | * | 5/2008 | Sinderby et al. ........ 128/204.21 |
| 2008/0236590 A1 | * | 10/2008 | Reissmann .......... 128/207.14 |
| 2008/0264419 A1 | * | 10/2008 | Lomask ............ A61M 16/0051 128/204.23 |
| 2008/0308104 A1 | * | 12/2008 | Blomberg ........... A61M 16/00 128/204.23 |
| 2009/0159082 A1 | | 6/2009 | Eger |
| 2009/0277448 A1 | * | 11/2009 | Ahlmen ............ A61M 16/0051 128/204.21 |
| 2010/0078024 A1 | * | 4/2010 | Andrieux .......... A61M 16/0051 128/204.21 |
| 2010/0095961 A1 | * | 4/2010 | Tornesel ........... A61M 16/0051 128/203.12 |
| 2010/0256513 A1 | | 10/2010 | Gumery et al. |
| 2011/0126834 A1 | * | 6/2011 | Winter ............ A61M 16/0808 128/204.22 |
| 2016/0303340 A1 | * | 10/2016 | Sinderby ........... A61M 16/204 |

FOREIGN PATENT DOCUMENTS

| | | |
|---|---|---|
| CN | 1 973 766 | 6/2007 |
| CN | 101 160 148 | 4/2008 |
| CN | 101 337 101 | 1/2009 |
| DE | 10 118 605 | 6/2002 |
| WO | 2002/002169 | 1/2002 |
| WO | 2006/053446 | 5/2006 |
| WO | 2010/022513 | 3/2010 |

* cited by examiner

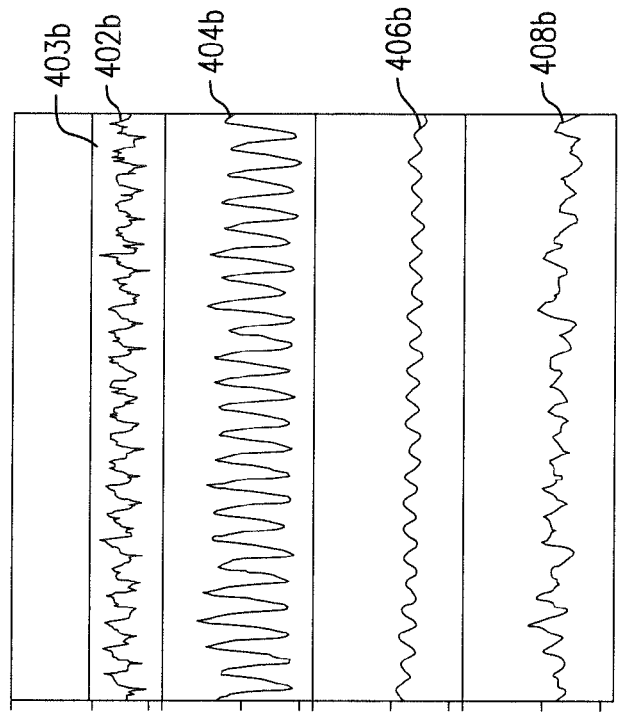
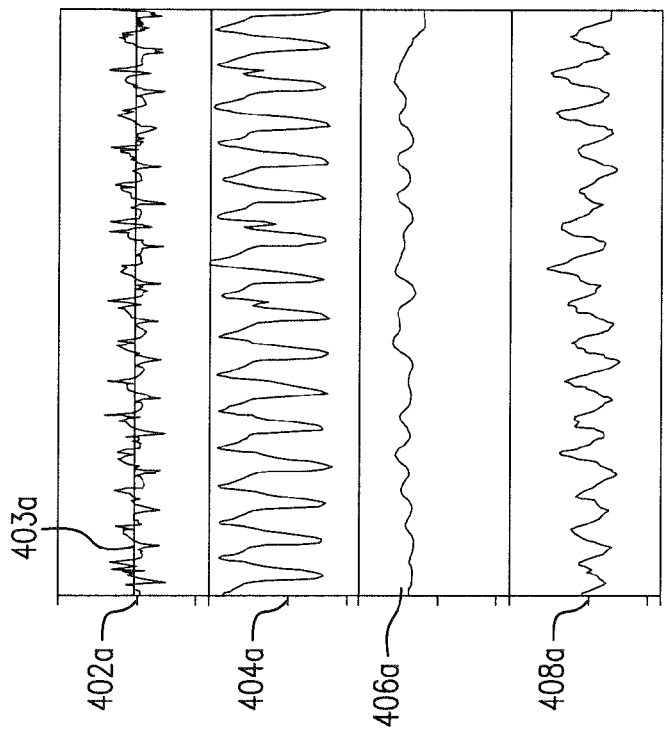
FIG.4A
FIG.4B

METHOD AND SYSTEM FOR PATIENT-SYNCHRONIZED VENTILATORY ASSIST WITH ENDOTRACHEAL THROUGH-FLOW

TECHNICAL FIELD

The present disclosure relates to the field of ventilatory assist systems. More specifically, the present disclosure relates to a method and a system for patient-synchronized ventilatory assist with endotracheal through-flow.

BACKGROUND

A recurring problem in patients with impaired function of the respiratory system is that the volume of air-exchanging lung parenchyma is reduced. This may be due to either edema, lung collapse and/or other factors. If a volume of air-transporting parenchyma/airways, comprising for example the main bronchi, trachea, and upper airways is maintained, the volume of air-exchanging parenchyma decreases relative to that of the air-transporting parenchyma/airways. In situations of increased need for $CO_2$ removal, a ventilatory contribution may be hampered if a dead space, or dead volume, in an air-transporting parenchyma/airways and in a respiratory circuit for a mechanical ventilator, becomes abnormally large relative to a proportion of the lungs with intact air-exchanging parenchyma. Consequently, $CO_2$ removal is hampered and arterial $CO_2(PaCO_2)$ may increase. This causes the tidal volume and ventilation to increase in order to maintain a tolerable level of arterial pressure ($PaCO_2$).

Until today, efforts have been made to minimize dead space, or dead volume, introduced in the respiratory circuit of mechanical ventilators. However actual tubes, for example endotracheal tubes, and other devices of conventional mechanical ventilators used to administer respiratory assist to a patient use single lumen designs and contribute to dead space ventilation. For that reason, $CO_2$ removal cannot be optimized.

Previous attempts to improve $CO_2$ removal from endotracheal tubes include multi-lumen designs aimed at introducing an air flow through a side lumen to eliminate $CO_2$ from a main lumen. An example of such design may be found in U.S. Pat. No. 5,291,882. The proposed approach, which uses parallel lumens, does not eliminate completely the volume of air re-breathed by the patient during inspiration. Thus the proposed approach reduces, but does not optimize the $CO_2$ removal and minimize the $CO_2$ re-breathing problem. Moreover, problems of dynamic hyperinflation due to constant inspiratory flow has also complicated this approach. Other approaches using tube lumens with valve functions may increase risk of occlusion.

Therefore, there is a need for improvements leading to further reduction or elimination of dead space induced by the respiratory circuit of a mechanical ventilator.

SUMMARY

According to the present disclosure, there is provided a patient-synchronized ventilatory assist system. The ventilatory assist system comprises a tube for connection to a patient's airway, an inspiratory tube lumen connected to the tube, an expiratory tube lumen connected to the tube, an inspiratory air source connected to the inspiration tube lumen, and a controller of the pressure in the expiratory tube lumen. The pressure controller is responsive to a physiological breathing signal representative of patient's inspiratory effort. Based on the physiological breathing signal, the pressure controller allows an unrestricted air flow through the expiratory tube lumen during a patient's expiration phase and partially restricts the air flow through the expiratory tube lumen to a minimum air flow during a patient's inspiration phase. During both the patient's inspiration and expiration phases, a unidirectional air flow is produced through the inspiratory tube lumen and the expiratory tube lumen to prevent air expired by the patient from being breathed again.

According to the present disclosure, there is also provided a patient-synchronized ventilatory assist method. The method comprises supplying an air flow in an inspiratory tube lumen of a tube connected to a patient's airway and, in response to a physiological breathing signal representative of patient's inspiratory effort, controlling an air flow in an expiratory tube lumen of the tube connected to the patient's airway. Controlling the air flow allows an unrestricted air flow through the expiratory tube lumen during a patient's expiration phase. Controlling the air flow also partially restricts the air flow through the expiratory tube lumen to a minimum air flow during a patient's inspiration phase. During both the patient's inspiration and expiration phases, a unidirectional air flow is produced through the inspiratory tube lumen and the expiratory tube lumen to prevent air expired by the patient from being breathed again.

The foregoing and other features will become more apparent upon reading of the following non-restrictive description of illustrative embodiments thereof, given by way of example only with reference to the accompanying drawings.

BRIEF DESCRIPTION OF THE DRAWINGS

Embodiments of the disclosure will be described by way of example only with reference to the accompanying drawings, in which:

FIG. 4a is a graph of experimental recordings of physiological respiratory parameters illustrating operation of a conventional ventilator system;

FIG. 4b is a graph of experimental recordings of physiological respiratory parameters using the double-lumen endotracheal tube and pressure control system of FIGS. 1 and 2;

DETAILED DESCRIPTION

Figure 1:
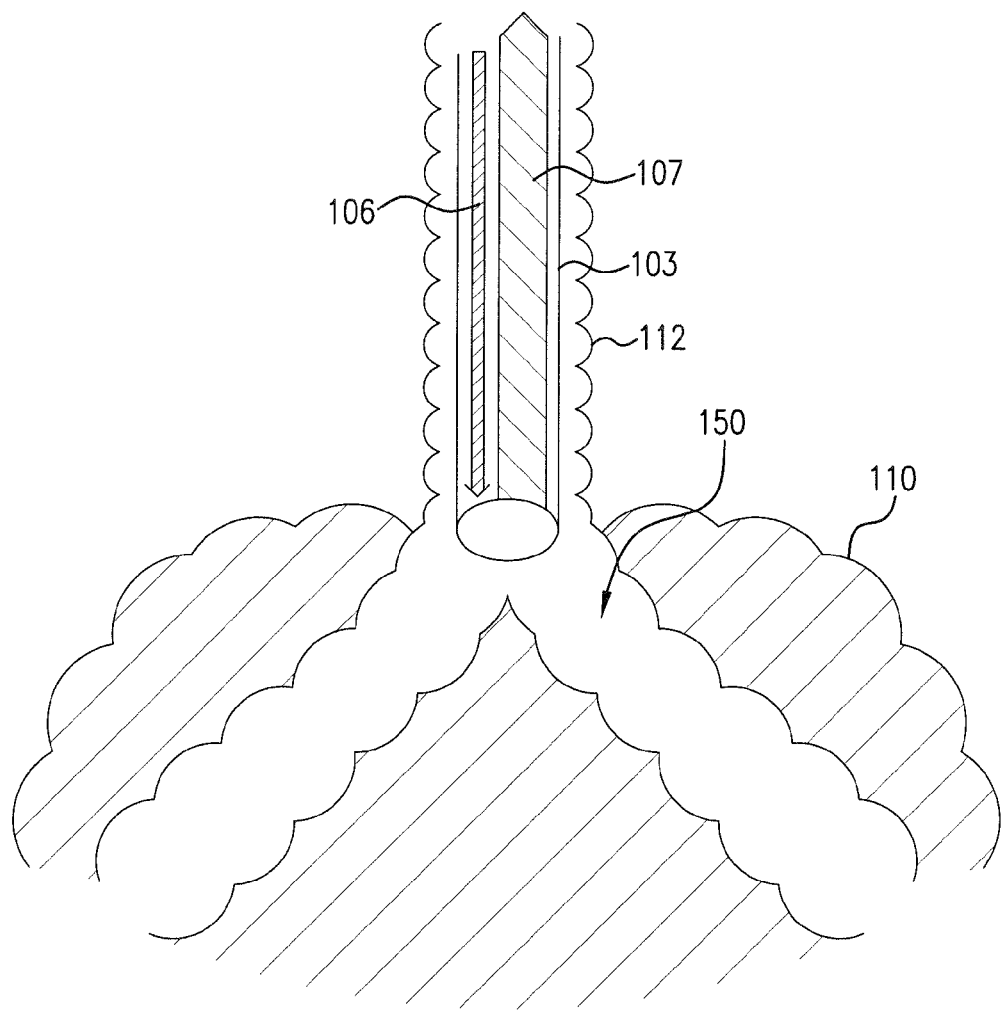
FIG. 1 is a side cross sectional, partial view of an example of double-lumen endotracheal tube showing intratracheal pulmonary ventilation.

Various aspects of the present disclosure generally address one or more of the problems related to the presence of dead space induced by respiratory circuits of mechanical ventilators. The present disclosure also relates to a ventilatory assist system and method including a feature of reduction of anatomical dead space in a patient's airways.

The following terminology is used throughout the present disclosure:

Ventilatory assist system: Apparatus adapted for medical use for assisting a patient in need of respiratory support.

Airway: Of a patient, lungs, bronchi, trachea, pharynx, nose and mouth, through which air is breathed.

Air: Any gas composition suitable for use in a ventilatory assist system. In the context of the present disclosure, the term "air" may refer to natural air, pure oxygen, natural air enriched with added oxygen, oxygen mixed with another gases such as water vapor, or any combination thereof. This term may also refer to air expelled from a patient's lungs, for example natural air containing additional $CO_2$ and humidity.

Lumen: A bore of a tube, for example a respiratory tube. A given tube may comprise a plurality of lumens.

Physiological signal: A measurable biometric quantity capable of being transmitted, for example as an electrical signal. such as the physiological breathing signal, generated by respiratory muscles.

Inspiratory effort: Voluntary or involuntary exertion of a breathing patient. This may be quantified as a neural measure.

Restricted/unrestricted: In the context of the present disclosure, an air flow present in a tube, lumen, or like conduit may be subject to a variable resistance, or restriction. It is well-known to those skilled in the art of fluid mechanics that any conduit will apply at least a minimum resistance to a flow. The terms "unrestricted" and "restricted" should be understood as relative terms expressing, respectively, a lower and a higher resistance to an air flow.

Minimum air flow: A partially restricted, non-zero air flow.

Endotracheal: Of a tube adapted for placement into a patient's trachea.

Synchrony: Time-wise correspondence between events.

A result of the reduction and elimination of dead space induced by the respiratory circuit of a mechanical ventilator is a reduction of respiratory drive, tidal volumes and ventilation, for example in critically ill patients. In this manner, mechanical ventilation may be used to efficiently unload the patient's respiratory system and respiratory muscles. Also, ventilatory $CO_2$ removal is optimized due to the reduction of dead space, limiting $CO_2$ rebreathing, which in turn reduces metabolic load.

The ventilatory assist system and method introduced herein supply ventilatory assist during inspiration via an endotracheal tube structured for delivering a separate, unidirectional inspiratory air flow into the patient's trachea via a first inspiratory tube lumen and a separate, unidirectional expiratory air flow from the patient's trachea through a second expiratory tube lumen. Also, a unidirectional flow of air is produced and maintained through the inspiratory tube lumen and the expiratory tube lumen; in this manner, ventilatory circuit dead space is eliminated, anatomical dead space is substantially reduced and washing out of $CO_2$ is optimized.

In an aspect, mechanical ventilation may be synchronized with patient's effort to breathe. For example, a physiological breathing signal is used to regulate the ventilatory assist in synchrony with patient's neural inspiration effort, thereby unloading and compensating for weak respiratory muscles.

Turning now to the appended drawings, FIG. 1 is a side cross sectional, partial view of an example of double-lumen endotracheal tube showing intratracheal pulmonary ventilation. A double-lumen endotracheal tube 103 shown on FIG. 1 forms part of a mechanical ventilator system for delivering air to the lungs 110 of a patient via the trachea 112. Schematically shown in FIG. 1 are an inspiratory flow in direction 106 toward the patient's lungs 110 and an expiratory flow in direction 107 away from the patient's lungs 110, through the double-lumen endotracheal tube 103 inserted into the trachea 112. Direction 106 is shown as a narrow arrow while direction 107 is shown as a thick arrow; this should be understood as a schematic manner of illustrating that the inspiratory flow in direction 106 originates from a smaller-diameter inspiratory tube lumen (also shown in FIG. 3) while the expiratory flow in direction 107 is directed through a larger-diameter expiratory tube lumen (also shown in FIG. 3).

Figure 2:
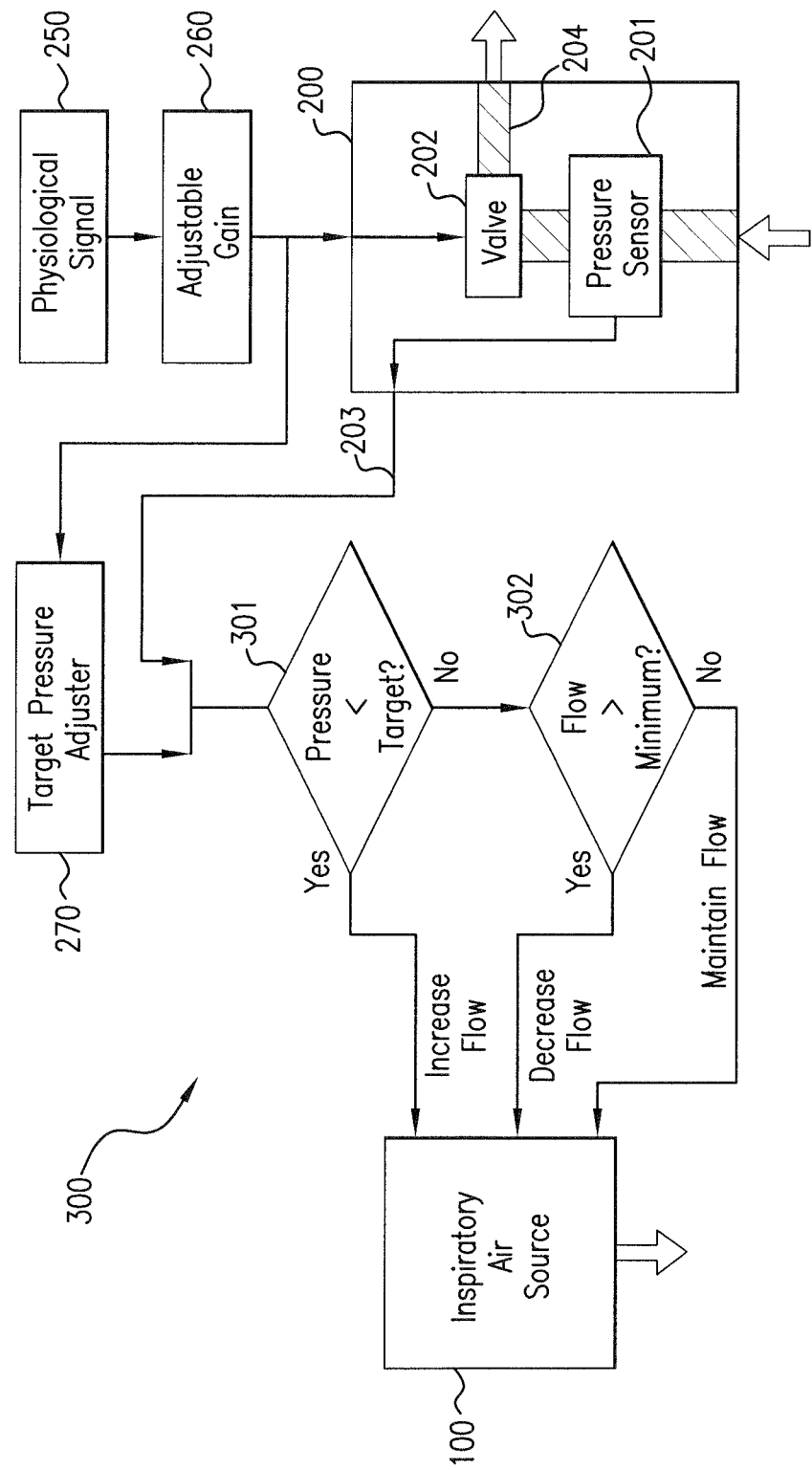
FIG. 2 is block diagram of an exemplary pressure control system for use with the double-lumen endotracheal tube of FIG. 1.
Figure 3:
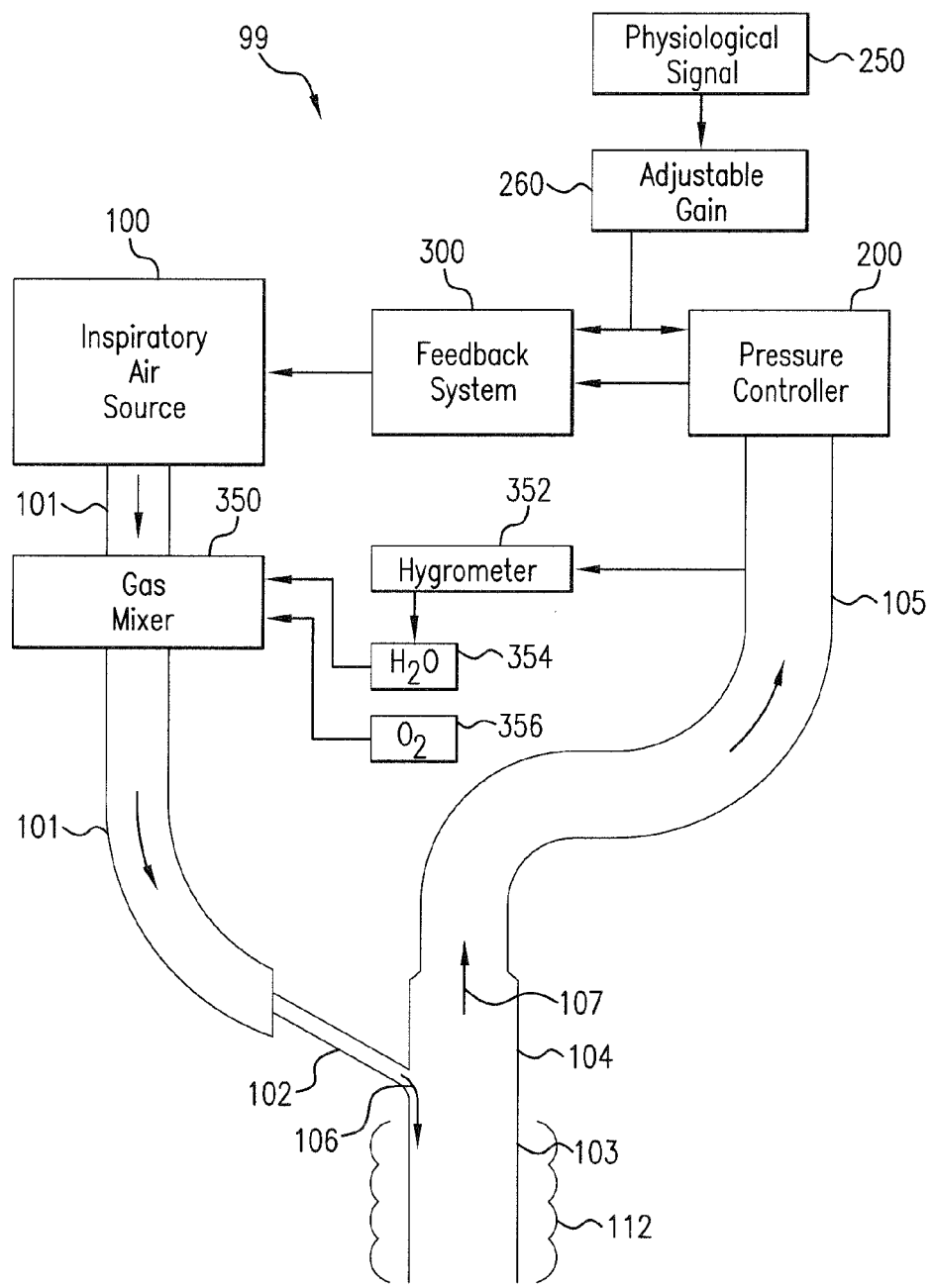
FIG. 3 is an example of connection of the double-lumen endotracheal tube of FIG. 1 with the pressure control system of FIG. 2.

FIG. 2 is block diagram of an exemplary pressure control system for use with the double-lumen endotracheal tube of FIG. 1. FIG. 3 is an example of connection of the double-lumen endotracheal tube of FIG. 1 with the pressure control system of FIG. 2. Therefore, the following description will refer to FIGS. 2 and 3 concurrently.

An inspiratory air source 100 is connected to an inspiratory line 101 and generates an air pressure, volume or flow to produce a target air flow through the inspiratory line 101. The inspiratory line 101 is in turn connected to an inspiratory tube lumen 102 of the double-lumen endotracheal tube 103 that is inserted into the patient's trachea 112. The inspiratory tube lumen 102 may be a single or multiple lumen.

A second lumen of the double-lumen endotracheal tube 103, hereinafter referred to as an expiratory tube lumen 104, is connected to an expiratory line 105 connected to a pressure controller 200. The pressure controller 200 may include a pressure sensor 201 and a valve 202 connected to an exhaust 204. A similar system for regulating air flow through the expiratory tube lumen 104 and the expiratory line 105 may be used instead of the controller 200 as shown. The pressure controller 200 may be feedback operated to produce and maintain a given pressure in the expiratory tube lumen 104 and the expiratory line 105. As will be described in more detail in the following description, the valve 202 may be controlled by a physiological breathing signal 250 for synchronizing the air flow through the expiratory tube lumen 104 and the expiratory line 105 with this physiological breathing signal 250. The pressure controller 200 operates in such a manner that the valve 202 restricts, but does not completely occlude the expiratory line 105 such that a minimum outward air flow remains present in the expiratory tube lumen 104 and the expiratory line 105 during the patient's inspiratory phase. Modulation of the restriction of the air flow through the expiratory tube lumen 104 allows adjustment of the pressure in the respiratory circuit of the mechanical ventilator to be proportional to the physiological breathing signal 250. A lowest pressure limit may be manually set to ensure sufficient positive end-expiratory pressure (PEEP) to maintain lung recruitment during neural expiration.

More specifically, the inspiratory air source 100 generates a target air flow through the inspiratory line 101 and the inspiratory tube lumen 102. In turn, the pressure controller 200 regulates a pressure for controlling air flow escaping the trachea 112 and the patient's lungs 110 through the expiratory tube lumen 104 and the expiratory line 105; more specifically, the pressure controller uses the valve 202 to alter a resistance to air flow of the expiratory tube lumen 104 and expiratory line 105.

The problem of limiting air flow resistance through the expiratory tube lumen 104 and the expiratory line 105 is resolved by providing the expiratory tube lumen 104 with a diameter larger than that of the inspiratory tube lumen 102. The larger resistance to air flow of the smaller-diameter inspiratory tube lumen 102 causes a larger pressure drop. However, the effect of this larger pressure drop is compensated for by using the inspiratory air source 100 to generate a target air flow through the inspiratory tube lumen 102.

A feedback system 300 between the pressure controller 200 and the inspiratory air source 100 ensures that the target air flow through the inspiratory line 101 and inspiratory tube lumen 102 is adjusted to generate a preset target pressure in the trachea 112, the expiratory tube lumen 104 and the expiratory line 105. The feedback system 300 comprises a first comparator 301 and an optional second comparator used as a minimum flow detector 302. The comparator 301 may receive a target pressure signal from a target pressure adjuster 270.

The target pressure adjuster 270 is responsive to the physiological breathing signal 250 to adjust the level of a target pressure. The physiological breathing signal 250 is a physiological signal as defined hereinabove. It may be reliably obtained as a measure of the electrical activation of the patient's diaphragm (EAdi), obtained for example using a method as described in U.S. Pat. Nos. 5,671,752, 5,820, 560, 6,588,423 and 6,901,286. The physiological breathing signal 250 may alternatively take the form of an electromyogram (EMG) signal obtained at the level of the alea of the nose (EMG-AN) of the patient, or at the thorax level (EMG-THO) of the patient. Biometric signals from the phrenical nerve of the patient, surface EMG, or measures of chest wall movements of the patient may also be used. Of course any other suitable physiological breathing signal 250 indicative of inspiratory effort including onset detection of the inspiratory effort, before the generation of inspiratory flow occurs, may be used. For example, the target pressure adjuster 270 may increase the level of the target pressure when the level of the physiological breathing signal 250 increases, indicating an increase of the patient's inspiratory effort. In the same manner, the adjuster 270 may decrease the level of the target pressure when the level of the physiological breathing signal 250 decreases, indicating a decrease of the patient's inspiratory effort. In fact, the target pressure may be adjusted by the target pressure adjuster 270 in proportion to the level of patient's inspiratory activity as indicated by the level of the physiological breathing signal 250 or in any other manner beneficial to patient's inspiratory assist. In an embodiment, the target pressure may further be set to ensure sufficient positive end-expiratory pressure (PEEP). Obviously, the target pressure adjuster 270 may also be set at a single level independent of the physiological breathing signal 250.

Operation of the feedback system 300 follows the following rules:
The target air flow through the inspiratory line 101 and inspiratory tube lumen 102 is increased when the comparator 301 detects that the pressure reading 203 from the pressure sensor 201 of the pressure controller 200, indicative of the pressure in the trachea 112, expiratory tube lumen 104 and expiratory line 105 during the patient's inspiration phase is lower than a target pressure, which may be set according to a target pressure signal from the target pressure adjuster 270.
The target air flow through the inspiratory line 101 and inspiratory tube lumen 102 is decreased when the comparator 301 detects that the pressure reading 203 from the pressure sensor 201 of the pressure controller 200, indicative of the pressure in the trachea 112, expiratory tube lumen 104 and expiratory line 105 during the patient's inspiration phase is higher than the target pressure from the target pressure adjuster 270, and also if it is higher than the manually set PEEP level. Before decreasing the target air flow through the inspiratory line 101 and inspiratory tube lumen 102, the minimum flow detector 302 ensures that the inspiratory air source 100 maintains a target air flow, through the inspiratory line 101 and inspiratory tube lumen 102, that is at least equal to or higher than a minimum value. If not, the target air flow through the inspiratory line 101 and inspiratory tube lumen 102 is maintained. The minimum value used in the minimum flow detector 302 for the target air flow is selected to be sufficient to ensure continuous washing out of $CO_2$.

Operation of the pressure control system 300 may be synchronized using the physiological breathing signal 250. More specifically, the valve 202 of the pressure controller 200 will partially close when the physiological breathing signal 250 indicates patient's inspiratory effort to allow the target air flow from the inspiratory line 101 and the inspiratory tube lumen 102 to build up a pressure in the endotracheal tube 103, the expiratory tube lumen 104 and the expiratory line 105 in order to assist inspiration of the patient. The valve 202 is partially closed to maintain a minimum air flow through the expiratory tube lumen 104 and the expiratory line 105 to contribute to, if not completely eliminate, substantially reduce ventilatory circuit dead space and anatomical dead space, and ensure continuous washing out of $CO_2$. When the physiological breathing signal 250 no longer indicates inspiratory effort of the patient, the valve 202 is opened to an extent that allows the patient to expire through the double-lumen endotracheal tube 103, the expiratory tube lumen 104, the expiratory line 105, the valve 202 and the exhaust 204 while maintaining a certain level of expiratory pressure to prevent, for example, collapse of the lungs.

It should be understood that, during both the inspiration and expiration phases, a unidirectional air flow is produced through the inspiratory line 101, the inspiratory tube lumen 102, the expiratory tube lumen 104 and the expiratory line 105 to prevent air expired by the patient to be breathed again. In this manner, ventilatory circuit dead space and anatomical dead space are, if not completely eliminated, substantially reduced and continuous washing out of $CO_2$ is ensured.

In an embodiment, a gain adjuster 260 may alter the physiological breathing signal 250 to adjust the level of the pressure in the trachea 112, expiratory tube lumen 104 and expiratory line 105, and thereby adjust the level of ventilatory assistance to the patient. For example, the adjustable gain 260 may be manually set by the medical personnel. Automatic adjustment of the gain 260 may also be contemplated, for example to obtain a target level of ventilatory assistance or physiological breathing signal 250.

Some options, amongst others, to deliver inspiratory assist to the patient are the following:
A target pressure or volume may be supplied to the patient during inspiration.
As explained in the foregoing description, the target pressure may be adjusted by the target pressure adjuster 270 in proportion to the level of patient's inspiratory activity as indicated by the level of the physiological breathing signal 250 or in any other manner beneficial to patient's inspiratory assist.
A mathematical model may be used for calculating a pressure loss within the endotracheal tube 103 based on a known air flow resistance and the diameters of the endotracheal tube 103, the expiratory tube lumen 104 and the expiratory line 105, and on a measurement of the air flow through these endotracheal tube 103, the expiratory tube lumen 104 and the expiratory line 105. The calculated pressure loss may then serve as the target pressure used by the comparator 301.

Another option is to directly measure a pressure at the free, proximal end of the endotracheal tube 103 inserted into the patient's trachea 112, near the tracheal bifurcation 150 (FIG. 1), and use this pressure as the target pressure of the comparator 301.

Oxygen from an oxygen source 356 may be injected in the inspiratory line 101 through a gas mixer 350 to enrich the target air flow through the inspiratory line 101 and inspiratory tube lumen 102.

To ensure adequate humidification, a humidity sensor (hygrometer) 352 may be used to detect humidity in the expiratory line 105 and, in response to the detected humidity, control a humidifier 354 connected to the gas mixer 350 to humidify, whenever needed, the target air flow through the inspiratory line 101 and the inspiratory tube lumen 102.

FIG. 4a is a graph of experimental recordings of physiological respiratory parameters illustrating operation of a conventional ventilator system. The graph of FIG. 4a may be compared with the graph of FIG. 4b, which is a graph of experimental recordings of physiological respiratory parameters using the double-lumen endotracheal tube and pressure control system of FIGS. 1 and 2. Both FIGS. 4a and 4b show recordings of air flow (402a, 402b), pressure (404a, 404b), and endtidal carbon dioxide (406a, 406b), measured in the expiratory line 105. FIGS. 4a and 4b also show recordings of diaphragm electrical activity (EAdi (408a, 408b)).

In the case of FIG. 4a, the air flow is bidirectional (inspiration and expiration) during each breathing cycle. It may be observed that the flow (402a) is above a zero line (403a) during inspiration phases and below the zero line (403a) during expiration phases. This produces a dead space in a breathing tube (not shown) of the conventional ventilator system, corresponding to a volume of an expiratory line and tube lumen. Consequently, a volume of expired air from the lungs is returned to the lungs during the next inspiration.

The graph of FIG. 4b illustrates recordings obtained using the double-lumen endotracheal tube 103 and pressure control system 300 of FIGS. 1 and 2, wherein no air from the expiratory tube lumen 104 and the expiratory line 105 is returned to the patient's lungs 110. The air flow (402b) is unidirectional from the patient's lungs 110 towards the atmosphere and constantly remains below a zero line (403b). No volume of expired air from the patient's lungs 110 is returned to the lungs during the next inspiration.

It may be observed that, in FIG. 4b, the endtidal carbon dioxide (406b) level is markedly reduced, compared to the corresponding level (406a) of FIG. 4a, during respiratory assist with the double-lumen endotracheal tube 103 and pressure control system 300 of FIGS. 1 and 2. It may also be observed that the diaphragm electrical activity (408b) and delivered pressure (404b) are reduced in FIG. 4b, compared to corresponding readings (408a, 404a) of FIG. 4a, although the ventilator system settings are the same. It may further be observed that generation of the pressure (404b) is synchronized with the diaphragm electrical activity (408b).

A comparison of the graphs of FIGS. 4a and 4b shows that the double-lumen endotracheal tube 103 and pressure control system 300 of FIGS. 1 and 2 may unload the patient's respiratory muscles by delivering ventilatory assist that is synchronized to the neural inspiratory effort (EAdi (408b)) both in terms of timing and pressure generation. Moreover, dead space may be minimized, and the metabolic load may be reduced (lower ETCO2, 406b) thereby further reducing respiratory drive (EAdi (408b)).

Figure 5:
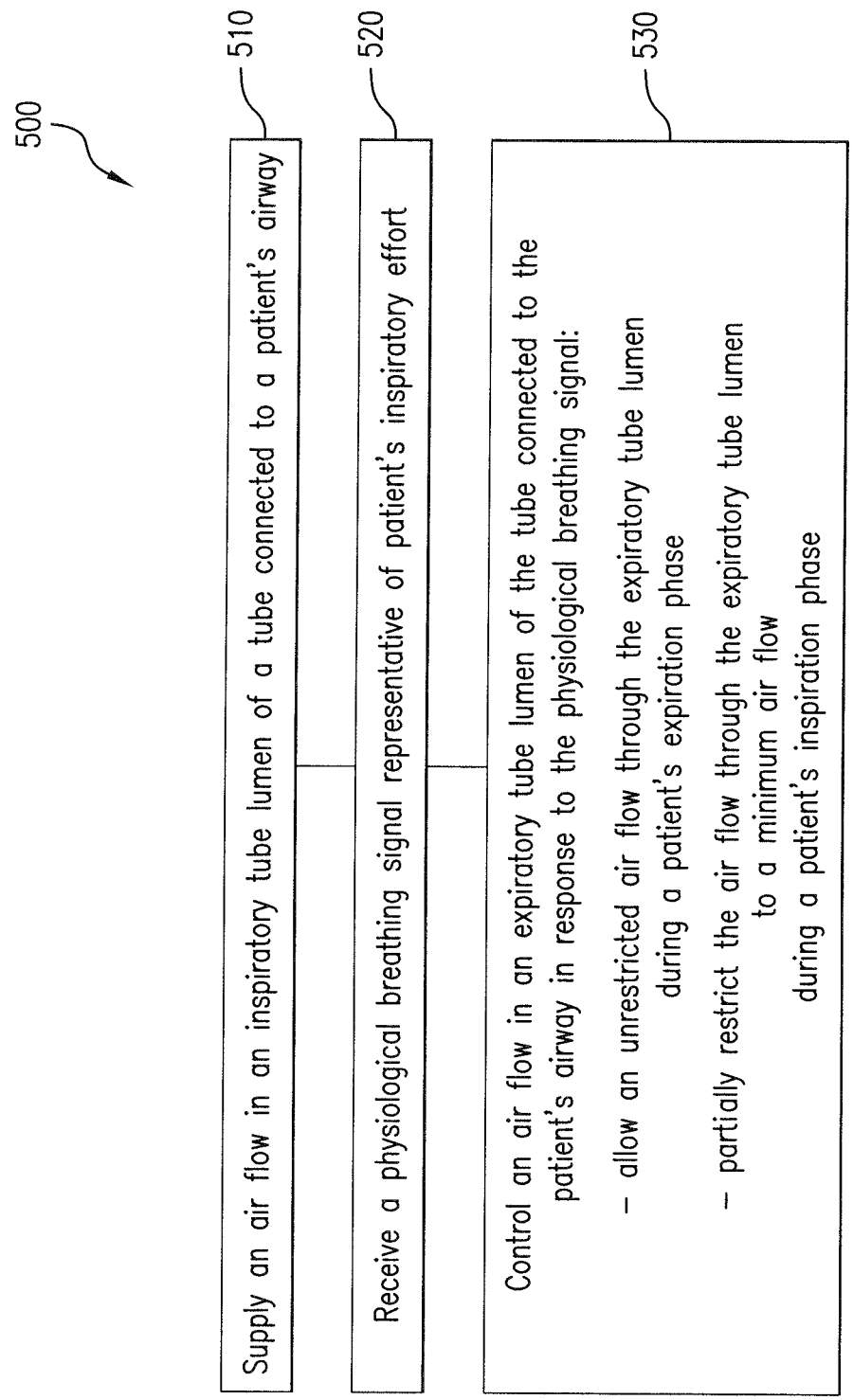
FIG. 5 is a flow chart of exemplary steps of a ventilatory assist method, capable of reducing neural inspiratory drive of a patient.

FIG. 5 is a flow chart of exemplary steps of a ventilatory assist method, capable of reducing neural inspiratory drive of a patient. Steps of a sequence 500 may be applied to a ventilatory assist system disclosed in the foregoing description given in relation to FIGS. 1, 2 and 3. In operation 510, an air flow is supplied in the inspiration tube lumen 102 of the tube 103 connected to the patient's airways. In response to a physiological signal representative of the patient's inspiratory effort, received in operation 520, control of the air flow in an expiratory tube lumen 102 of the tube 103 connected to the patient's airway is made in operation 530. The control made in operation 530 is such that during the patient's inspiratory phase, the air flow through the expiratory tube lumen 104 connected to the patient's airways is partially restricted. In contrast, during the patient's expiratory phase, the air flow is unrestricted to allow expiratory flow from the patient's trachea 112 to evacuate through the endotracheal tube 103, the expiratory tube lumen 104, and thereby through the expiratory line 105.

A result of the control made in operation 530 is that during both the patient's inspiration and expiration phases, a unidirectional air flow is produced through the inspiratory tube lumen 102 and the expiratory tube lumen 104 to prevent air expired by the patient from being breathed again.

Control of the air flow made in operation 530 may for example be made by actuating the valve 202 of FIG. 2.

Figure 6:
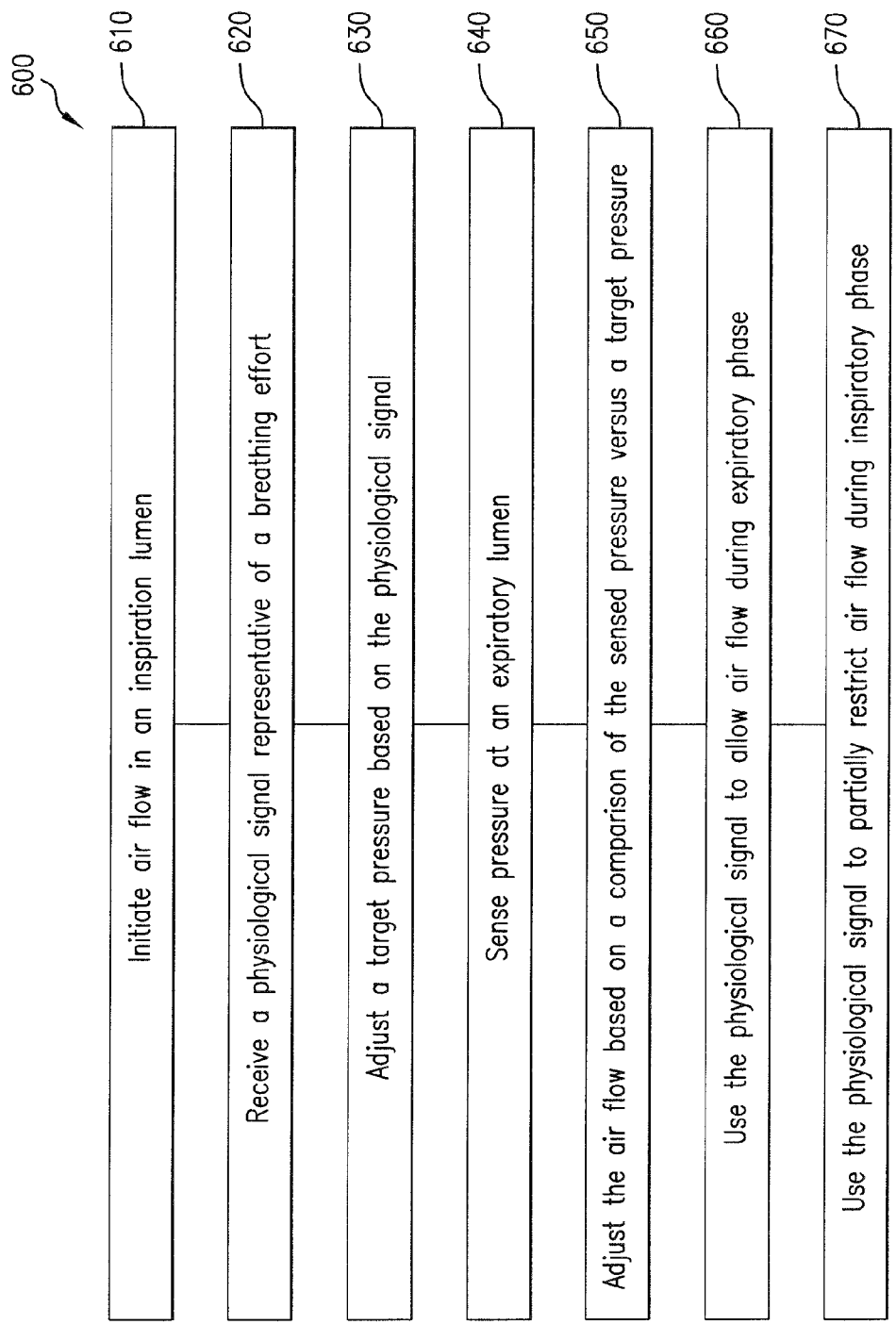
FIG. 6 is a flow chart of other aspects of the ventilatory assist method of FIG. 5.

FIG. 6 is a flow chart of other aspects of the ventilatory assist method of FIG. 5. It should be understood that the operations of the sequence 600 of FIG. 6 may also be applied in a ventilatory assist system as described in connection with the description of FIGS. 1, 2 and 3. More specifically, the sequence 600 comprises:

Operation 610: A target air flow is produced by the inspiratory air source 100 through the inspiratory tube lumen 101 and the inspiratory line 102.

Operation 620: The physiological breathing signal 250 representative of inspiratory effort of the patient is received by the pressure control system 300.

Operation 630: The target pressure adjuster 270 adjusts a target pressure in response to the physiological breathing signal 250.

Operation 640: Pressure in the endotracheal tube 103, the expiratory tube lumen 104 and the expiratory line 105 is sensed, or detected, through pressure sensor 201.

Operation 650: The target air flow produced by the inspiratory air source 100 in the inspiratory line 101 and the inspiratory tube lumen 102 is adjusted, or controlled, as a function of a comparison by the comparator 301 between the pressure detected in the endotracheal tube 103, the expiratory tube lumen 104 and the expiratory line 105 and the target pressure from the adjuster 270.

Operation 660: The physiological breathing signal 250 is used to control air flow through the expiratory tube lumen 104 and the expiratory line 105 by controlling opening of the valve 202, thereby altering a pressure in the double-lumen endotracheal tube 103, the expiratory tube lumen 104 and the expiratory line 105 in synchrony with the patient's inspiratory effort as indicated by the physiological breathing signal 250. In operation 660, when the physiological breathing signal 250 indicates an expiratory phase, the valve 202 is opened to an extent to allow the patient to expire through the double-lumen endotracheal tube 103, the expiratory tube lumen 104, the expiratory line 105, the valve 202 and the exhaust 204 while maintaining a certain level of expiratory pressure to prevent, for example, collapse of the lungs during that expiratory phase.

Operation 670: When the physiological breathing signal 250 indicates an inspiratory phase, the valve 202 will partially close to increase resistance to air flow through the expiratory tube lumen 104 and the expiratory line 105 to allow the target air flow from the inspiratory line 101 and the inspiratory tube lumen 102 to build up a pressure in the endotracheal tube 103, the expiratory tube lumen 104 and the expiratory line 105 in order to assist inspiration of the patient. The valve 202 is partially closed to maintain a minimum air flow through the endotracheal tube 103, the expiratory tube lumen 104 and the expiratory line 105 to contribute to eliminate ventilatory circuit dead space and substantially reduce anatomical dead space, and ensure continuous washing out of $CO_2$.

Those of ordinary skill in the art will realize that the description of the devices and methods for patient-synchronized ventilatory assist are illustrative only and are not intended to be in any way limiting. Other embodiments will readily suggest themselves to such persons with ordinary skill in the art having the benefit of the present disclosure. Furthermore, the disclosed patient-synchronized ventilatory assist may be customized to offer valuable solutions to existing needs and problems of ventilatory assist systems.

In the interest of clarity, not all of the routine features of the implementations of patient-synchronized ventilatory assist systems and methods are shown and described. It will, of course, be appreciated that in the development of any such actual implementation of the patient-synchronized ventilatory assist systems and methods, numerous implementation-specific decisions may need to be made in order to achieve the developer's specific goals, such as compliance with application-, system- and business-related constraints, and that these specific goals will vary from one implementation to another and from one developer to another. Moreover, it will be appreciated that a development effort might be complex and time-consuming, but would nevertheless be a routine undertaking of engineering for those of ordinary skill in the field of ventilatory assist systems having the benefit of the present disclosure.

In accordance with the present disclosure, the components, process steps, and/or signal structures described herein may be implemented using various types of operating systems, computing platforms, network devices, computer programs, and/or general purpose machines. In addition, those of ordinary skill in the art will recognize that devices of a less general purpose nature, such as hardwired devices, field programmable gate arrays (FPGAs), application specific integrated circuits (ASICs), or the like, may also be used. Where a method comprising a series of process steps is implemented by a computer or a machine and those process steps may be stored as a series of instructions readable by the machine, they may be stored on a tangible medium.

Systems and modules described herein may comprise software, firmware, hardware, or any combination(s) of software, firmware, or hardware suitable for the purposes described herein. Software and other modules may reside on servers, workstations, personal computers, computerized tablets, personal digital assistants (PDA), and other devices suitable for the purposes described herein. Software and other modules may be accessible via local memory, via a network, via a browser or other application or via other means suitable for the purposes described herein. Data structures described herein may comprise computer files, variables, programming arrays, programming structures, or any electronic information storage schemes or methods, or any combinations thereof, suitable for the purposes described herein.

Although the present disclosure has been described hereinabove by way of non-restrictive, illustrative embodiments thereof, these embodiments may be modified at will within the scope of the appended claims without departing from the spirit and nature of the present disclosure.

What is claimed is:

1. A ventilatory assist system, comprising:
    a tube for connection to a patient's airway, the tube including (a) an inspiratory tube lumen with a proximal end in fluid communication with the patient's airway and a distal end, and (b) an expiratory tube lumen with a proximal end in fluid communication with the patient's airway and the proximal end of the inspiratory tube lumen, and a distal end in fluid communication with an exhaust;
    an inspiratory air source connected to the distal end of the inspiratory tube lumen for supplying air flow to the inspiratory tube lumen; and
    a pressure controller connected to the expiratory tube lumen and using a physiological breathing signal having a level indicative of an inspiratory effort of the patient to indicate expiration and inspiration phases of the patient during breathing cycles of the patient to establish, during each of the breathing cycles, (a) an expiratory pressure in the expiratory tube lumen during the patient's expiration phase to allow patient's expiration through the expiratory tube lumen while producing a first unidirectional air flow from the inspiratory air source through the inspiratory tube lumen, the expiratory tube lumen and the exhaust, and (b) an inspiratory assist pressure in the expiratory tube lumen during the patient's inspiration phase to allow the inspiratory air source to provide ventilatory assist to the patient through the inspiratory tube lumen and the patient's airway while producing a second unidirectional air flow from the inspiratory air source through the inspiratory tube lumen, the expiratory tube lumen and the exhaust;
    wherein the first and second unidirectional air flows prevent air expired by a patient from being breathed again; and
    wherein the pressure controller uses the physiological breathing signal to synchronize the expiratory pressure and the inspiratory assist pressure with the expiration and inspiration phases of the breathing cycles of the patient.

2. The ventilatory assist system of claim 1, wherein:
    the pressure controller comprises a valve disposed between the distal end of the expiratory tube lumen and the exhaust, and controlled using the physiological breathing signal.

3. The ventilatory assist system of claim 2, wherein:
    the valve is partially closed during the patient's inspiration phase to establish the inspiratory assist pressure while producing the second unidirectional air flow.

4. The ventilatory assist system of claim 1, wherein:
    the physiological breathing signal is a measure of electrical activation of a patient's diaphragm (EAdi).

5. The ventilatory assist system of claim 1, further comprising:

a pressure sensor for sensing a pressure in the expiratory tube lumen; and a feedback system interposed between the pressure sensor and the inspiratory air source.

6. The ventilatory assist system of claim 5, wherein:

the feedback system comprises a comparator of the pressure sensed by the pressure sensor in the expiratory tube lumen to a target pressure.

7. The ventilatory assist system of claim 6, comprising:

a target pressure adjuster for setting the target pressure in response to the physiological breathing signal.

8. The ventilatory assist system of claim 6, wherein:

the inspiratory air source is adapted to increase an air flow through the inspiratory tube lumen in response to a detection by the comparator that the pressure sensed by the pressure sensor in the expiratory tube lumen is lower than the target pressure.

9. The ventilatory assist system of claim 5, wherein:

the feedback system comprises a minimum flow detector for maintaining at least a minimum air flow through the inspiratory tube lumen.

10. The ventilatory assist system of claim 9, wherein:

the inspiratory air source is adapted to maintain at least the minimum air flow in response to a signal from the minimum flow detector.

11. The ventilatory assist system of claim 1, wherein:

the tube is an endotracheal tube.

12. The ventilatory assist system of claim 1, wherein:

the inspiratory tube lumen is a smaller-diameter tube lumen and the expiratory tube lumen is a larger-diameter tube lumen.

13. The ventilatory assist system of claim 1, comprising:

a gas mixer connected between the inspiratory air source and the distal end of the inspiratory tube lumen.

14. The ventilatory assist system of claim 13, comprising:

an oxygen source connected to the gas mixer.

15. The ventilatory assist system of claim 13, comprising:

a hygrometer connected to the expiratory tube lumen; and a humidifier controlled by the hygrometer and connected to the gas mixer.

16. The ventilatory assist system of claim 1, comprising:

a gain adjuster interposed between a source of the physiological breathing signal and the pressure controller for adjusting a level of ventilatory assist to the patient.

17. The ventilatory assist system of claim 1, wherein the pressure controller is responsive to the physiological breathing signal to establish the expiratory pressure in the expiratory tube lumen in proportion to the patient's inspiratory effort.

18. A ventilatory assist method, comprising:

connecting a tube to a patient's airway, the tube including (a) an inspiratory tube lumen with a proximal end in fluid communication with the patient's airway and a distal end, and (b) an expiratory tube lumen with a proximal end in fluid communication with the patient's airway and the proximal end of the inspiratory tube lumen, and a distal end in fluid communication with an exhaust;

supplying an air flow to the distal end of the inspiratory tube lumen; and using a physiological breathing signal having a level indicative of an inspiratory effort of the patient to indicate expiration and inspiration phases of the patient during breathing cycles of the patient, establishing during of the each breaching cycles (a) an expiratory pressure in the expiratory tube lumen during the patient's expiration phase to allow patient's expiration through the expiratory tube lumen and the exhaust while producing a first unidirectional air flow through the inspiratory tube lumen, the expiratory tube lumen and the exhaust, and (b) an inspiratory assist pressure in the expiratory tube lumen during the patient's inspiration phase to provide ventilatory assist to the patient through the inspiratory tube lumen and the patient's airway while producing a second unidirectional air flow through the inspiratory tube lumen, the expiratory tube lumen and the exhaust;

wherein the first and second unidirectional air flows prevent air expired by a patient from being breathed again; and wherein the expiratory pressure and the inspiratory assist pressure are synchronized with the expiration and inspiration phases of the breathing cycles of the patient.

19. The method of claim 18, comprising:

sensing a pressure in the expiratory tube lumen; and adjusting the air flow in the inspiratory tube lumen based on a comparison between the pressure sensed in the expiratory tube lumen and a target pressure.

20. The method of claim 19, wherein:

adjusting the air flow in the inspiratory tube lumen comprises increasing the air flow in the inspiratory tube lumen when the pressure sensed in the expiratory tube lumen is lower than the target pressure and decreasing the air flow in the inspiratory tube lumen when the pressure sensed in the expiratory tube lumen is higher than the target pressure.

21. The method of claim 19, comprising:

adjusting the target pressure based on the physiological breathing signal.

22. The method of claim 18, wherein the expiratory pressure in the expiratory tube lumen is established in proportion to the patient's inspiratory effort.

\* \* \* \* \*